US010913699B2

(12) United States Patent
Nelson et al.

(10) Patent No.: US 10,913,699 B2
(45) Date of Patent: Feb. 9, 2021

(54) METHOD OF RECOVERING PHENOL FROM A BPA PRODUCTION PLANT AND THE PLANT FOR RECOVERING THE SAME

(71) Applicant: SABIC GLOBAL TECHNOLOGIES B.V., Bergen op Zoom (NL)

(72) Inventors: Mark Erik Nelson, Mt. Vernon, IN (US); Ahmed Abouelfetouh Youssef, Mt. Vernon, IN (US); Karl Aaron Baro, Mt. Vernon, IN (US); Paulus Johannes Maria Eijsbouts, Bergen op Zoom (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/502,124

(22) Filed: Jul. 3, 2019

(65) Prior Publication Data

US 2019/0322606 A1     Oct. 24, 2019

Related U.S. Application Data

(62) Division of application No. 15/751,190, filed as application No. PCT/US2016/046151 on Aug. 9, 2016, now Pat. No. 10,407,370.

(Continued)

(51) Int. Cl.
*C07C 37/72*   (2006.01)
*C07C 37/68*   (2006.01)
(Continued)

(52) U.S. Cl.
CPC ............. *C07C 37/72* (2013.01); *C07C 37/20* (2013.01); *C07C 37/685* (2013.01); *C07C 37/74* (2013.01);
(Continued)

(58) Field of Classification Search
CPC ......... C07C 37/08; C07C 37/20; C07C 37/72; C07C 37/74; C07C 37/685; C07C 39/06;
(Continued)

(56) References Cited

U.S. PATENT DOCUMENTS 5,545,764 A    8/1996  Berg et al.
6,806,394 B2 * 10/2004  Evitt ....................... C07C 37/84
                                                             568/728

(Continued)

FOREIGN PATENT DOCUMENTS

JP    3775832 B2       4/1997
JP    H09110766 H      4/1997

OTHER PUBLICATIONS

International Search Report for International Application No. PCT/US2016/046151; International Filing date Aug. 9, 2016; dated Nov. 7, 2016; 7 pages.

(Continued)

*Primary Examiner* — Yate' K Cutliff
(74) *Attorney, Agent, or Firm* — Cantor Colburn LLP (57)  ABSTRACT

In an embodiment, a method of recovering phenol comprises heating a preheater inlet stream in a preheater to form a splitter inlet stream; separating the splitter inlet stream into a splitter top outlet stream and a splitter bottom outlet stream in a splitter column; separating the splitter bottom outlet stream into a crude top outlet stream and a crude bottom outlet stream in a crude phenol column; hydro-extracting the crude top outlet stream in a hydro-extractor column to form an extractor primary outlet stream; recovering a product phenol outlet stream from the extractor primary outlet stream in a finishing column; combining a bisphenol A plant phenol recovery stream from a bisphenol A reaction from a bisphenol A phenol purification system with the preheater inlet stream, the splitter inlet stream, the splitter bottom (Continued)

outlet stream, the crude top outlet stream, or a combination comprising at least one of the foregoing.

16 Claims, 2 Drawing Sheets

Related U.S. Application Data (60) Provisional application No. 62/217,126, filed on Sep. 11, 2015.

(51) Int. Cl.
*C07C 37/20* (2006.01)
*C07C 37/74* (2006.01)
*C07C 37/82* (2006.01)
*C07C 39/06* (2006.01)
*C07C 39/16* (2006.01)
*B01D 53/00* (2006.01)
*B01J 8/00* (2006.01)

(52) U.S. Cl.
CPC ............ *C07C 37/82* (2013.01); *C07C 39/06* (2013.01); *C07C 39/16* (2013.01); *B01D 53/00* (2013.01); *B01J 8/005* (2013.01)

(58) Field of Classification Search
CPC .. C07C 39/15; C07C 39/16; C02F 1/26; B01J 8/005; B01D 53/00
See application file for complete search history.

(56) References Cited

U.S. PATENT DOCUMENTS

| | | |
|---|---|---|
| 6,972,345 B2 | 12/2005 | Blaschke et al. |
| 8,143,456 B2 | 3/2012 | Young et al. |
| 9,255,053 B2 | 2/2016 | Palmer et al. |
| 2004/0249224 A1 | 12/2004 | Kumbhar et al. |
| 2008/0281129 A1 | 11/2008 | Palmer |
| 2010/0105960 A1 | 4/2010 | Evitt et al. |
| 2014/0121417 A1 | 5/2014 | Youssef et al. |
| 2017/0240496 A1 | 8/2017 | Nelson et al. |
| 2018/0258020 A1 | 9/2018 | Nelson et al. |

OTHER PUBLICATIONS

Noureldin et al.; "Global energy targets and optimal operating conditions for waste energy recovery in Bisphenol-A plant"; Applied Thermal Engineering 26 (2006); pp. 374-381.
Written Opinion of the International Search Report for International Application No. PCT/US2016/046151; International Filing date Aug. 9, 2016; dated Nov. 7, 2016; 12 pages.

* cited by examiner

METHOD OF RECOVERING PHENOL FROM A BPA PRODUCTION PLANT AND THE PLANT FOR RECOVERING THE SAME

CROSS-REFERENCE TO RELATED APPLICATIONS

This application is a divisional of U.S. application Ser. No. 15/751,190, filed Feb. 2, 2018, which is a national stage application of International Application No. PCT/US2016/046151, filed Aug. 9, 2016, which claims benefit of U.S. Provisional Application No. 62/217,126, filed Sep. 11, 2015, all of which are incorporated herein by reference in their entirety.

TECHNICAL FIELD

This disclosure relates to a method of recovering phenol in a BPA production plant and the plant for recovering the same.

BACKGROUND

Bisphenol A (BPA) is a high production volume compound with a world-wide estimated annual production of over 2 million tons. The demand for this compound is primarily due to its use as a monomer in the production of many high commodity materials such as epoxies and polycarbonates. The general process, by which BPA is produced, involves the condensation reaction of acetone with two equivalents of phenol in the presence of an acid catalyst or a sulfonated polystyrene resin. This reaction is often performed in an excess of phenol in order to help ensure full condensation. As a result, in a BPA production plant, the product stream comprises the excess phenol. This excess phenol can be recovered and either recycled back to the BPA production plant or used for a different process.

There remains a need in the art for a process, which can more efficiently recover phenol from a BPA plant.

BRIEF DESCRIPTION

Disclosed herein is a method of recovering phenol in a BPA production plant and the plant for recovering the same.

In an embodiment, a method of recovering phenol from a bisphenol A production facility comprises reacting phenol and acetone in the presence of a catalyst to produce a bisphenol A stream comprising bisphenol A; separating the bisphenol A stream into a product bisphenol A stream and a purge stream comprising an unreacted phenol; separating the purge stream into a primary top outlet stream and a primary bottom outlet stream in a primary distillation column; adding an acid catalyst via acid stream to the primary bottom outlet stream to form a cracker inlet stream; separating the cracker inlet stream into a cracker top outlet stream and a cracker bottom outlet stream in the acid-cracker; separating the cracker top outlet stream and the cracker bottom outlet stream into a secondary top outlet stream and a secondary bottom outlet stream in a secondary recovery column; forming a bisphenol A plant phenol recovery stream comprising at least a portion of the primary top outlet stream, at least a portion of the cracker top outlet stream, at least a portion of the secondary top outlet stream, or a combination comprising at least one of the foregoing; combining the bisphenol A plant phenol recovery stream with a stream of a phenol purification plant selected from a preheater inlet stream, a splitter inlet stream, a splitter bottom outlet stream, a crude top outlet stream, or a combination comprising at least one of the foregoing.

In another embodiment, a method of recovering phenol comprises heating a preheater inlet stream comprising cumene, phenol, and acetone in a preheater to form a splitter inlet stream; separating the splitter inlet stream comprising the cumene, the phenol, and the acetone into a splitter top outlet stream comprising the acetone and the cumene and a splitter bottom outlet stream comprising the phenol in a splitter column; separating the splitter bottom outlet stream into a crude top outlet stream comprising the phenol and a crude bottom outlet stream comprising the cumene in a crude phenol column; hydro-extracting the crude top outlet stream in a hydro-extractor column to form an extractor primary outlet stream comprising the phenol; recovering a product phenol outlet stream, comprising the phenol in a concentration of greater than 99.5 wt % based on the total weight of the product phenol outlet stream, from the extractor primary outlet stream in a finishing column; combining a bisphenol A plant phenol recovery stream from a bisphenol A reaction comprising 95 to 99 wt % of a recovered phenol from a bisphenol A phenol purification system with the preheater inlet stream, the splitter inlet stream, the splitter bottom outlet stream, the crude top outlet stream, or a combination comprising at least one of the foregoing.

In another embodiment, a system for recovering phenol comprises a phenol purification system and a bisphenol A production facility. The phenol purification system comprises a preheater, a splitter column, a crude phenol column, a hydro-extractor column, and a finishing column. The preheater comprises a preheater inlet and a preheater outlet. The splitter column comprises a splitter inlet in fluid communication with the preheater outlet, a splitter top outlet, and a splitter bottom outlet. The crude phenol column comprises a crude inlet in fluid communication with the splitter bottom outlet, a crude top outlet, and a crude bottom outlet. The hydro-extractor column comprises an extractor inlet in fluid communication with the crude top outlet, an extractor outlet, and an extractor primary outlet. The finishing column comprises a finisher inlet in fluid communication with the extractor primary outlet, a product phenol outlet, and a finisher bottom outlet. The bisphenol A production facility comprises a bisphenol A reactor, a bisphenol A separation unit, a primary distillation column, an acid-cracker, and a secondary recovery column. The bisphenol A reactor comprises a reactor inlet and a reactor outlet. The bisphenol A separation unit comprises a bisphenol A separation inlet in fluid communication with the reactor outlet, a bisphenol A separation first outlet, and a bisphenol A separation second outlet. The primary distillation column comprises a primary inlet in fluid communication with the bisphenol A separation first outlet, a primary top outlet, and a primary bottom outlet. The acid-cracker comprises a cracker inlet in fluid communication with the primary bottom outlet, a cracker top outlet, and a cracker bottom outlet. The secondary recovery column comprises a first inlet in fluid communication with the cracker top outlet, a second inlet in fluid communication with the cracker bottom outlet, a secondary top outlet, and a secondary bottom outlet. The primary top outlet, the cracker top outlet, the secondary top outlet, or a combination comprising at least one of the foregoing is in fluid communication with the preheater inlet, the splitter inlet, the crude inlet, the extractor inlet, or a combination comprising at least one of the foregoing.

The above described and other features are exemplified by the following figures and detailed description.

BRIEF DESCRIPTION OF THE DRAWINGS

Refer now to the figures, which are exemplary embodiments, and wherein the like elements are numbered alike.

DETAILED DESCRIPTION

Phenol purification from a typical BPA plant generally results in a maximum phenol purity of 99 weight percent (wt %), more specifically, a maximum of 98 wt % based on the total weight of the purified stream. It was unexpectedly discovered that the capability of the phenol purification section of a phenol production facility can be advantageously used to purify a phenol recovery stream in a BPA production facility. The benefits of purifying a phenol stream from the BPA production facility in a phenol purification section of a phenol production facility arise from the fact that the phenol purification section of a phenol production facility has a significantly greater throughput than that of a typical phenol purification section of a BPA production system, for example, of only 55 to 76 tons per year. Due to the increased throughput, the phenol purification can achieve one or both of a higher phenol purification, for example, a greater operating efficiency and/or a phenol purity of greater than or equal to 99 to 100 wt %, specifically, 99.5 to 100 wt %, specifically, 99.9 to 100 wt % based on the total weight of the phenol product stream. Thus, the operational and capital cost of these purification facilities can be reduced without negatively affecting the quality of the product streams generated in the facilities.

Unless specifically stated otherwise, the weight percent values used herein are based on the total weight of the respective stream.

Figure 1:
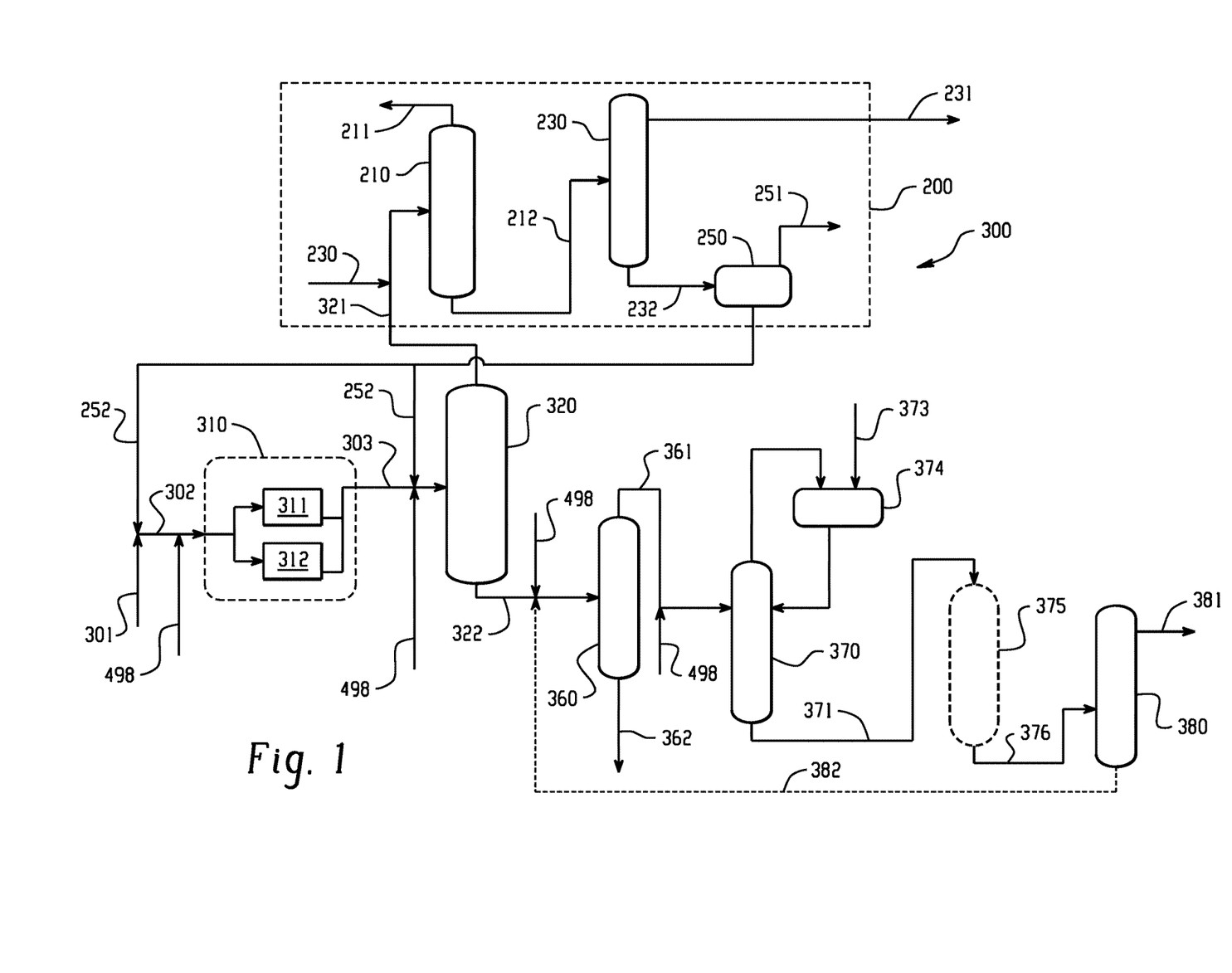
FIG. 1 is a schematic illustration of a phenol purification system of a phenol production plant.

An example of a reaction to produce phenol is via the cumene process. Here, a reaction mixture of benzene, propylene, and oxygen is reacted to produce a product mixture comprising acetone and phenol. A phenol purification system can be used to purify the product mixture, for example, as illustrated in FIG. 1. FIG. 1 is a schematic illustration of a phenol purification system 300 of a phenol production plant. The phenol purification system 300 can include a feed stream 301 comprising acetone and phenol. The feed stream 301 can further comprise non-phenol compounds from upstream phenol production processes such as water, cumene, dimethylbenzyl alcohol (DMBA), hydroxyacetone (HA), α-methylstyrene (AMS), AMS dimers, acetophenone (AP), acetaldehyde, cumyl phenols, phenolic resins, or a combination including at least one of the foregoing.

The feed stream 301 can be combined with one or both of an acetone purification recycle stream 252 containing phenol recovered from an acetone purification section 200 and BPA plant phenol recovery stream 498 to form a preheater inlet stream 302. The preheater inlet stream 302 can be heated in a preheater 310 by any suitable heating process. For example, preheater 310 can comprise preheater units 311 and 312 that operate in parallel. In this configuration, the preheater 310 can accommodate a higher flowrate while still heating the preheater inlet stream 302 to a desired temperature. It is noted that while it is illustrated that the three streams are combined prior to entering the preheater, the streams can be added in other configurations to the preheater.

The preheater 310 can be in fluid communication with a splitter column 320 via splitter inlet stream 303. Splitter inlet stream 303 can comprise 5 to 50 wt %, specifically, 10 to 40 wt %, more specifically, 20 to 30 wt % acetone. Unless otherwise stated, the weight percent values are relative to the total weight of the respective stream. Splitter inlet stream 303 can comprise 20 to 75 wt %, specifically, 30 to 60 wt %, more specifically 40 to 50 wt % phenol. The splitter inlet stream 303 can comprise 0 to 35 wt %, specifically, 5 to 30 wt % of a non-phenol compound. The preheater can be operated such that the splitter inlet stream 303 is heated to a temperature of greater than or equal to 90 degrees Celsius (° C.), for example, 90 to 180° C., or 90 to 150° C., or 100 to 135° C. The BPA plant phenol recovery stream 498 can be added to the splitter inlet stream 303 prior to entering the splitter column 320, or can be added separately. The splitter column 320 separates species of the splitter inlet stream 303 into a splitter top outlet stream 321 and a splitter bottom outlet stream 322 based on their volatility (e.g., the tendency of the species to vaporize at a given temperature which is related to the species vapor pressure). The splitter column 320 can include one or more distillation columns. The splitter column 320 can operate at a temperature of 90 to 150° C., specifically, 100 to 140° C. The splitter column 320 can operate at a pressure of 250 to 450 kilopascal (kPa), specifically, 300 to 400 kPa.

The splitter top outlet stream 321 can contain the high volatility species of the splitter inlet stream 303 including acetone. The splitter top outlet stream 321 can comprise 30 to 70 wt %, specifically, 40 to 60 wt % acetone. The splitter top outlet stream 321 can comprise 0 to 5 wt %, specifically, 0 to 1 wt % phenol. The splitter top outlet stream 321 can comprise 30 to 70 wt %, specifically, 40 to 60 wt % of non-phenol compounds such as cumene, α-methylstyrene, water, hydroxyacetone, acetaldehyde, or a combination comprising at least one of the foregoing. The splitter top outlet stream 321 can comprise 0 to 1 wt % of each of the following independently: dimethylbenzyl alcohol, paracumyl phenol, dicumyl phenol, hydroxyacetone, acetophenone, methanol, acetaldehyde, AMS dimer, and 2-methylbenzofuran. The splitter top outlet stream 321 can be recovered from the top of the splitter column 320 and fed to the acetone purification section 200 where an acetone product stream 231 can be recovered. The acetone product stream 231 can comprise greater than or equal to 95 wt % acetone, or 95 to 100 wt %, or, 97 to 99.99 wt %. The acetone purification section 200 can provide the acetone purification recycle stream 252 comprising phenol, which can be combined with the feed stream 301, combined with the splitter inlet stream 303, sent to a separate process, or a combination including at least one of the foregoing.

A splitter bottom outlet stream 322 can be recovered from the bottom of the splitter column 320. The splitter bottom outlet stream 322 can comprise lower volatility species of the splitter inlet stream 303 including phenol. The splitter bottom outlet stream 322 can comprise greater than or equal to 94 wt %, specifically, 95 to 99 wt %, more specifically, 97 to 99 wt % of phenol. The splitter bottom outlet stream 322 can comprise 0 to 4 wt % of α-methylstyrene. The splitter bottom outlet stream 322 can comprise 0 to 2 wt % of acetophenone. The splitter bottom outlet stream 322 can comprise 0 to 1 wt % of each of the following independently: acetone, cumene, α-methylstyrene, water, dimethylbenzyl alcohol, paracumyl phenol, dicumyl phenol, hydroxyacetone, acetophenone, methanol, acetaldehyde, 2-methylbenzofuran, and AMS dimers. The splitter bottom outlet stream 322 can be fed to a crude phenol column 360 where it can be separated into a crude top outlet stream 361 and a crude bottom outlet stream 362. The crude phenol column inlet stream can include the splitter bottom outlet stream 322, an optional finisher bottom outlet stream 382, the BPA plant phenol recovery stream 498, or a combination including at least one of the foregoing. The crude phenol column 360 can operate at a temperature of 100 to 300° C., specifically, 150 to 250° C. The crude phenol column 360 can operate at a pressure of 75 to 275 kPa, specifically, 100 to 225 kPa.

The crude phenol column 360 can include a distillation column, which can separate species present in the splitter bottom outlet stream 322 based on their volatility. The crude bottom outlet stream 362 can include lower volatility species present in the splitter bottom outlet stream 322 such as paracumyl phenol, dicumyl phenol, AP, AMS dimer, or a combination comprising at least one of the foregoing. For example, the crude bottom outlet stream 362 can contain dimethylbenzyl alcohol, acetophenone, AMS dimers, dicumyl phenol, paracumyl phenol (PCP), or a combination comprising at least one of the foregoing. The crude bottom outlet stream 362 can be recovered from the phenol purification system 300 for separate processing. The crude top outlet stream 361 can comprise 97 to 99.7 wt % of phenol.

The crude top outlet stream 361 can be fed to an extractor inlet of a hydro-extractor column 370. The crude top outlet stream 361 can be combined with the BPA plant phenol recovery stream 498 prior to entering the hydro-extractor column 370 or can be added separately. Water stream 373 containing water can be fed directly to the hydro-extractor column 370 or to a cooler 374 in fluid communication with the hydro-extractor column 370. The hydro-extractor column 370 can include a liquid-liquid extraction device, which can separate compounds based on their relative solubilities in two different immiscible liquid phases. Non-phenol compounds present in one liquid phase (e.g., a phenol rich phase) can be extracted to a second liquid phase (e.g., a water phase) where the non-phenol compound has a greater solubility. Water stream 373 can be used to extract non-phenol compound (e.g., alkylated benzenes) present in the crude top outlet stream 361.

The hydro-extractor column 370 can include internal structures to increase the interfacial area between the two liquid phases. These internal structures can include fixed plates, packing, or a combination including at least one of the foregoing. The hydro-extractor column 370 can be heated (e.g., through a heat exchanger in thermal communication with the hydro-extractor column 370). The hydro-extractor can operate in any suitable flow configuration such that interaction between the two immiscible liquid phases is ensured. For example, heat supplied to the hydro-extractor can buoy the water phase and drive counter-current flow of the two liquid phases within the hydro-extractor, where the phenol rich phase moves toward the bottom of the hydro-extractor while the water phase moves towards the top. The water phase can be cooled in the cooler 374 and returned to the hydro-extractor. The hydro-extractor column 370 can operate at a temperature of 30 to 100° C., specifically, 50 to 70° C. The hydro-extractor column 370 can operate at a pressure of 350 to 550 kPa, specifically, 400 to 500 kPa. At least a portion of the top stream exiting the hydro-extractor column 370 can be removed from the system, for example, upstream of or downstream of the cooler 374 and can optionally be recycled to an upstream unit such as one or both of splitter column 320 or crude phenol column 360.

The extractor primary outlet stream 371 can include the phenol rich phase including phenol and non-phenol compounds (e.g., dicumyl phenol, 2-methylbenzofuran (2-MBF), AP, or a combination comprising at least one of the foregoing). The extractor primary outlet stream 371 can comprise 98 to 99.999 wt % of phenol. Non-phenol compounds present in the extractor primary outlet stream 371 can include heteroatoms (e.g., 2-MBF) which can be alkylated to higher molecular mass species (e.g., greater molecular mass in comparison to the species having the heteroatom) in an optional ion exchanger 375. The effluent from the optional ion exchanger 375 can be fed along a finisher inlet stream 376 to a finishing column 380. The finishing column 380 can separate the finisher inlet stream 376 into a product phenol outlet stream 381 and a finisher bottom outlet stream 382. The finisher bottom outlet stream 382 can optionally be recycled and combined with the splitter bottom outlet stream 322. The finisher column 380 can include at least one distillation column. The product phenol outlet stream 381 can be recovered from the phenol purification system 300 and used in the manufacture of bisphenol-A (BPA) in a BPA production plant. The product phenol outlet stream 381 can comprise greater than or equal to 99.5 wt %, specifically, 99.5 to less than 100 wt % of phenol.

Figure 2:
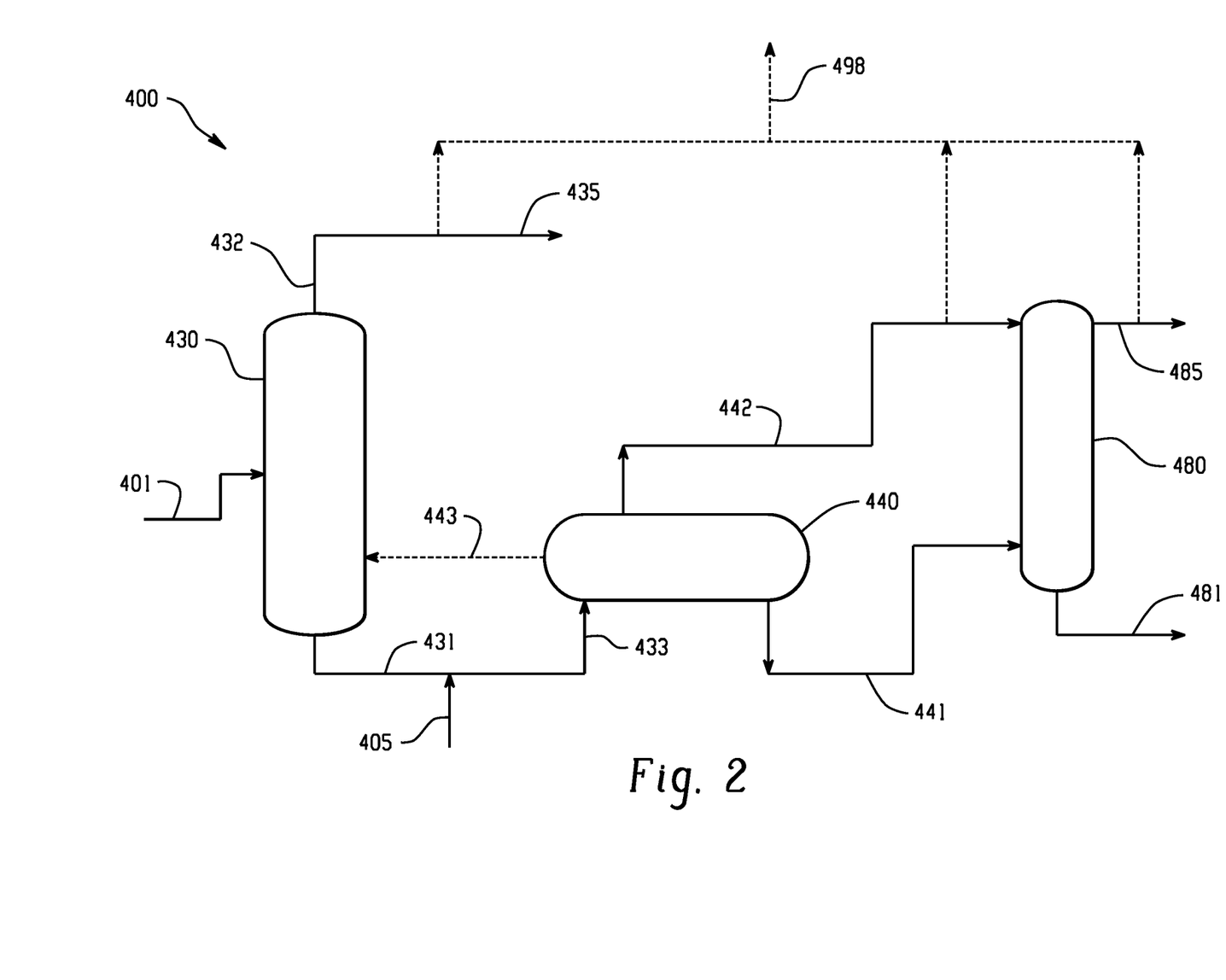
FIG. 2 is a schematic illustration of a phenol purification system of a BPA production plant.

FIG. 2 is a schematic illustration of a phenol purification system 400 of a BPA production plant. The phenol purification system 400 can include a primary distillation column 430 which can separate a purge stream 401 containing phenol and lower volatility compounds (also referred to as heavies) present in the BPA production process (e.g., including para-para BPA, ortho-para BPA, chroman, dimers, BPX-I, BPX-II, BPA-HVY, spirobi, IPP) into a primary top outlet stream 432 and a primary bottom outlet stream 431. As used herein chroman has the formula (I), dimers refer to compounds of the formulae (II) and (III) for linear dimers and of the formula (IV) for a cyclic dimer, BPX-1 has the formula (V), BPX-II has the formula (VI), spirobi has the formula (VII), IPP has the formula (VIII), and BPA-HVY has the formulae (IX-XIII).

The primary top outlet stream 432 can comprise phenol. The primary top outlet stream 432 can be recovered as a phenol recovery stream 435 for use within the BPA production process. The primary top outlet stream 432 can comprise 95 to 99 wt %, of phenol based on the total weight of the stream. The primary bottom outlet stream 431 can be combined with an acidic stream 405 that comprises an acid catalyst (e.g., dodecylbenzene sulfonic acid (DBSA)) to form a cracker inlet stream 433. The cracker inlet stream 433 can be fed to an acid-cracker 440 where heavies present in the primary bottom outlet stream 431 can be cracked and optionally returned to the primary column by cracker recycle stream 443. The primary distillation column 430 can operate at a temperature of 60 to 200° C., specifically, 75 to 110° C. and a pressure of 1 to 10 kPa, specifically, 2 to 8 kPa.

The acid-cracker 440 can include a cracker top outlet stream 442 containing vapor phase phenol and a cracker bottom outlet stream 441 containing liquid phase phenol and heavies (e.g., by-products and non-phenol compounds resultant from upstream processes). The cracker top outlet stream 442 can comprise 95 to 99 wt % phenol, specifically, 97 to 99 wt %. The acid-cracker 440 can operate at a temperature of 100 to 200° C., specifically, 130 to 180° C. and a pressure of 5 to 50 kPa, specifically, 10 to 30 kPa.

The cracker top outlet stream 442 can be fed to a secondary recovery column 480. The cracker bottom outlet stream 441 can be fed to the secondary recovery column 480. The secondary recovery column 480 can be a distillation column and can separate one or both of the cracker top outlet stream 442 and the cracker bottom outlet stream 441 into a secondary top outlet stream 485 containing phenol and a secondary bottom outlet stream 481 containing heavies which can include a tar product. The secondary top outlet stream 485 can comprise 95 to 99 wt % phenol.

The phenol rich streams, which can be recovered from the phenol purification system 400 of a BPA production plant and combined into the phenol purification system of the phenol production plant include the primary top outlet stream 432, the cracker top outlet stream 442, the secondary top outlet stream 485, or a combination including at least a portion of one or more of the foregoing. Thus, the BPA plant phenol recovery stream 498 can be in fluid communication with the primary top outlet stream 432, the cracker top outlet stream 442, the secondary top outlet stream 485, or a combination including at least one of the foregoing. Secondary top outlet stream 485 can be recycled to primary distillation column 430 and the BPA plant phenol recovery stream 498 can comprise primary top outlet stream 432.

The BPA plant phenol recovery stream 498 can be combined with the phenol purification system 300 in a number of locations. The BPA plant phenol recovery stream 498 can be combined with at least one of the preheater inlet stream 302, the splitter inlet stream 303, the splitter bottom outlet stream 322, the crude top outlet stream 361.

Combining the BPA plant phenol recovery stream 498 and the preheater inlet stream 302 can allow the streams to equilibrate prior to entering the splitter column 320. The preheater 310 can be a more efficient heat transfer device in comparison to the splitter column 320 (e.g., owed to lower heat loss, lower thermal resistance of the material of construction, or flow configuration), or the opposite can be the case. Thus, selecting between the preheater inlet stream 302 and the splitter inlet stream 303, or selecting how much of the BPA plant phenol recovery stream 498 is supplied to either location, can be influenced by heat transfer efficiency differences between the preheater 310 and the splitter column 320.

Combining the BPA plant phenol recovery stream 498 with the splitter bottom outlet stream 322 can reduce or eliminate the possibility that non-phenol compounds are transferred from the BPA production plant to the acetone product stream 231. Combining the BPA plant phenol recovery stream 498 with the extractor inlet stream (crude top outlet stream 361) can require less energy to heat the BPA plant phenol recovery stream 498 in comparison to the other locations to which the recovery stream can be fed (e.g., the preheater inlet stream 302, the splitter inlet stream 303, or the crude phenol column 360 inlet).

The phenol purification system 300 can further comprise an acetone purification system 200, where the splitter top outlet stream 321 can be purified in the acetone purification system 200. For example, the splitter top outlet stream 321 and caustic stream 230 can be added to a first acetone column 210 to form a first top stream 211 and a first bottom stream 212 comprising a purified acetone. A second acetone column 230 can also be added to the first acetone column 210. The first bottom stream 212 can be added to a second acetone column 230 to form a second bottom stream 232 and acetone product stream 231 comprising the purified product acetone. The acetone product stream 231 can comprise 99.5 to 99.9 wt % of acetone. The second bottom stream 232 can be separated in a separator 250, for example, in a decanter, to form decanted stream 251 comprising cumene and an acetone phenol recycle stream 252 that can be added to the preheater 310.

The method of recovering phenol in a BPA production plant can be done in a recovery system. For example, the system can comprise a phenol purification system 300 that purifies phenol produced in a phenol production facility and a BPA phenol purification system 400 of a bisphenol-A production plant. The phenol purification system 300 can comprise a preheater 310, a splitter column 320, a crude phenol column 360, a hydro-extractor column 370, an optional ion exchanger 375, and a finishing column 380. The preheater 310 can comprise a preheater inlet and a preheater outlet. The splitter column 320 can comprise a splitter inlet in fluid communication with the preheater outlet, a splitter top outlet, and a splitter bottom outlet. The crude phenol column 360 can comprise a crude inlet in fluid communication with the splitter bottom outlet, a crude top outlet, and a crude bottom outlet. The hydro-extractor column 370 can comprise an extractor inlet in fluid communication with the crude top outlet, an extractor outlet, and an extractor primary outlet. The hydro-extractor column 370 can comprise a cooler extractor inlet that can be in fluid communication with a cooler outlet of a cooler 374. The cooler 374 can further comprise a cooler inlet in fluid communication with the extractor outlet. The finishing column 380 can comprise a finisher inlet in fluid communication with the extractor primary outlet, a product phenol outlet, and a finisher bottom outlet. The finisher bottom outlet can optionally be in fluid communication with the crude inlet. The system can optionally comprise an optional ion exchanger 375 comprising an exchanger inlet in fluid communication with the extractor primary outlet and an exchanger outlet in fluid communication with the finisher inlet.

A bisphenol A production facility can comprise a bisphenol A reactor comprising a reactor inlet and a reactor outlet, and a bisphenol A separation unit comprising a bisphenol A separation inlet in fluid communication with the reactor outlet, a bisphenol A separation first outlet, and a bisphenol A separation second outlet. The bisphenol A separation first outlet can be in fluid communication with the BPA phenol purification system 400 comprising a primary distillation column 430, an acid-cracker 440, and a secondary recovery column 480. The primary distillation column 430 can comprise a primary inlet in fluid communication with the BPA separation first outlet, a primary top outlet, and a primary bottom outlet. The acid-cracker 440 can comprise a cracker inlet in fluid communication with the primary bottom outlet, a cracker top outlet, and a cracker bottom outlet. The secondary recovery column 480, for example, a distillation column can comprise a first inlet in fluid communication with the cracker top outlet, a second inlet in fluid communication with the cracker bottom outlet, a secondary top outlet, and a secondary bottom outlet. The acid-cracker 440 can further comprise a cracker recycle outlet and the primary distillation column 430 can further comprise a primary recycle inlet, and the cracker recycle outlet can be in fluid communication with the primary recycle inlet.

In the recovery system, the primary top outlet, the cracker top outlet, the secondary top outlet, or a combination comprising at least one of the foregoing, can be in fluid communication with the preheater inlet, the splitter inlet, the crude inlet, the extractor inlet, or a combination comprising at least one of the foregoing. For example, the primary top outlet, the cracker top outlet, the secondary top outlet, or a combination comprising at least one of the foregoing, can be in fluid communication with one or both of the preheater inlet and the splitter inlet. For example, the primary top outlet, the cracker top outlet, the secondary top outlet, or a combination comprising at least one of the foregoing, can be in fluid communication with one or both of the crude inlet and the extractor inlet.

Although the description of the process is directed to a continuous process, any one or more of the steps can be conducted batch-wise.

It will be appreciated by persons skilled in the art that the positioning of the various streams/lines as described herein as being, e.g., in the "top", "middle", "bottom", or "side" of a particular vessel (such as an acid-cracker, distillation column, extraction column, and the like) is relative because the actual position at which material is to be introduced or recovered is dependent on the conditions being maintained in the particular unit. For example, a stream entering the "bottom" of a column can actually enter several stages above the sump including the reboiler of the column, and a stream exiting the "top" of the column can actually exit several stages below the top stage including the condenser of the column. Thus, such terms herein are included for ease of reference to describe a general orientation regarding various columns and lines/streams and such terms are not meant to be limiting to one exact location. Also, although for illustrative purposes, the accompanying figures depict singular units, it is understood that multiple vessels can be used where suitable. Furthermore, multiple vessels can have any suitable flow arrangement such as serial, parallel, or a combination including at least one of the foregoing.

The following examples are provided to illustrate the present method. The examples are merely illustrative and are not intended to limit devices made in accordance with the disclosure to the materials, conditions, or process parameters set forth therein.

TABLE 1

| Condition/Composition | Stream 303 | Stream 321 | Stream 322 |
|---|---|---|---|
| Temperature (K) | 394.3 | 338.5 | 464.2 |
| Pressure (kN/m$^2$) | 347 | 460 | 160 |
| Vapor Fraction | 0 | 0 | 0 |
| Mole Flow (kmol/s) | 0.452 | 0.316 | 0.136 |
| Mass Flow (kg/s) | 27.447 | 14.488 | 12.959 |
| Volume Flow (m$^3$/s) | 0.033 | 0.018 | 0.014 |
| Flow rate (kg/h) | | | |
| Acetone | 7.395 | 7.395 | trace |
| Phenol | 12.749 | 0.063 | 12.687 |
| Cumene | 3.513 | 3.513 | trace |
| α-methylstyrene | 0.684 | 0.684 | trace |
| Dimethylbenzyl alcohol | 0.095 | trace | 0.095 |
| Water | 2.730 | 2.730 | trace |
| Paracumyl phenol | 0.049 | trace | 0.049 |
| Dicumyl Phenol | 0.069 | trace | 0.069 |
| Hydroxyacetone | 0.096 | 0.096 | trace |
| Acetophenone | 0.042 | trace | 0.042 |
| Methanol | trace | trace | trace |
| Acetaldehyde | 0.005 | 0.005 | trace |
| 2-methylbenzofuran | trace | trace | trace |
| AMS dimer | 0.018 | trace | 0.018 |

TABLE 3

| Condition/Composition | Stream 322 | Stream 361 | Stream 362 |
|---|---|---|---|
| Temperature (K) | 464.2 | 330.7 | 478.5 |
| Pressure (kN/m$^2$) | 160 | 460 | 294 |
| Vapor Fraction | 0 | 0 | 0 |
| Mole Flow (kmol/s) | 0.136 | 0.138 | 0.002 |
| Mass Flow (kg/s) | 12.959 | 12.953 | 0.264 |
| Volume Flow (m$^3$/s) | 0.014 | 0.012 | <0.001 |
| Mass Flow (kg/s) | | | |

TABLE 3-continued

| Condition/Composition | Stream 322 | Stream 361 | Stream 362 |
|---|---|---|---|
| Acetone | — | — | — |
| Phenol | 12.687 | 12.953 | 0.04 |
| Cumene | trace | — | — |
| α-methylstyrene | trace | trace | trace |
| Dimethylbenzyl alcohol | 0.095 | trace | 0.047 |
| Water | trace | trace | trace |
| Paracumyl phenol | 0.049 | trace | 0.049 |
| Dicumyl phenol | 0.069 | <0.001 | 0.069 |
| Hydroxyacetone | trace | trace | trace |
| Acetophenone | 0.042 | trace | 0.042 |
| Methanol | — | — | — |
| Acetaldehyde | — | — | — |
| 2-methylbenzofuran | trace | trace | trace |
| AMS Dimer | 0.018 | trace | 0.018 |

TABLE 2

| Condition/Composition | Stream 303 | Stream 498 | Stream 321 | Stream 322 |
|---|---|---|---|---|
| Temperature (K) | 394.3 | 353.1 | 338.6 | 464.2 |
| Pressure (kN/m$^2$) | 350 | 500 | 460 | 160 |
| Vapor Fraction | 0 | 0 | 0 | 0 |
| Mole Flow (kmol/s) | 0.452 | 0.001 | 0.317 | 0.137 |
| Mass Flow (kg/s) | 27.447 | 0.130 | 14.556 | 13.020 |
| Volume Flow (m$^3$/s) | 0.033 | <0.001 | 0.018 | 0.014 |
| Mass Flow (kg/s) | | | | |
| Acetone | 7.395 | — | 7.395 | trace |
| Phenol | 12.749 | 0.127 | 0.131 | 12.746 |
| Cumene | 3.513 | — | 3.513 | trace |
| α-methylstyrene | 0.684 | — | 0.684 | trace |
| Dimethylbenzyl alcohol | 0.095 | — | trace | 0.095 |
| Water | 2.730 | <0.001 | 2.731 | trace |
| Paracumyl phenol | 0.049 | — | trace | 0.049 |
| Dicumyl phenol | 0.069 | — | trace | 0.069 |
| Hydroxyacetone | 0.096 | — | 0.096 | trace |
| Acetophenone | 0.042 | — | trace | 0.042 |
| Methanol | trace | — | trace | trace |
| Acetaldehyde | 0.005 | — | 0.005 | trace |
| 2-methylbenzofuran | — | — | — | — |
| AMS Dimer | 0.018 | — | trace | 0.018 |
| para-para BPA | — | 0.001 | trace | 0.001 |
| ortho-para BPA | — | <0.001 | trace | <0.001 |
| Chroman | — | <0.001 | trace | <0.001 |
| Dimers | — | <0.001 | trace | <0.001 |
| BPX-I | — | <0.001 | trace | <0.001 |
| BPX-II | — | trace | trace | trace |
| BPA-HVY | — | 0.001 | trace | 0.001 |
| Spirobi | — | trace | trace | trace |
| IPP | — | <0.001 | trace | <0.001 |

EXAMPLES

Computer simulations were performed for the splitter column 320, the crude phenol column 360 and the hydro-extractor of the phenol purification system 300 of a phenol production plant operated with various feed stream compositions. The computer simulations were run using Aspen Plus to determine the relative concentrations of various streams in the present phenol purification plant. In the tables, K is Kelvin, kN/m$^2$ is kilonewtons per meter squared, kmol/s is kilomoles per second, kg/s is kilograms per second, m$^3$/s is meters cubed per second, and kg/h is kilograms per hour.

In the tables, trace refers to components present in amount of less than 10$^{-9}$ kg/h; - - refers to components that were not present in the stream; and <0.0001 refers to components that were present in an amount of 10$^{-9}$ kg/h to less than 0.0001 kg/h.

TABLE 4

| Condition/Composition | Stream 322 | Stream 498 | Stream 361 | Stream 362 |
|---|---|---|---|---|
| Temperature (K) | 464.2 | 353.1 | 330.7 | 478.6 |
| Pressure (kN/m$^2$) | 160 | 500 | 460 | 294 |
| Vapor Fraction | 0 | 0 | 0 | 0 |
| Mole Flow (kmol/s) | 0.136 | 0.001 | 0.139 | 0.002 |
| Mass Flow (kg/s) | 12.959 | 0.130 | 13.083 | 0.266 |
| Volume Flow (m$^3$/s) | 0.014 | <0.001 | 0.013 | <0.001 |
| Mass Flow (kg/s) | | | | |
| Acetone | — | — | — | — |
| Phenol | 12.687 | 0.127 | 13.082 | 0.040 |
| Cumene | trace | — | — | — |
| α-methylstyrene | trace | — | trace | trace |
| Dimethylbenzyl alcohol | 0.095 | — | trace | 0.047 |
| Water | trace | <0.001 | <0.001 | trace |
| Paracumyl phenol | 0.049 | — | trace | 0.049 |
| Dicumyl phenol | 0.069 | — | <0.001 | 0.069 |
| Hydroxyacetone | trace | — | trace | trace |
| Acetophenone | 0.042 | — | trace | 0.042 |
| Methanol | — | — | — | — |
| Acetaldehyde | — | — | — | — |
| 2-methylbenzofuran | trace | — | trace | trace |
| AMS Dimer | 0.018 | — | trace | 0.018 |
| para-para BPA | — | 0.001 | trace | 0.001 |
| ortho-para BPA | — | <0.001 | trace | <0.001 |
| Chroman | — | <0.001 | trace | <0.001 |
| Dimers | — | <0.001 | trace | <0.001 |
| BPX-I | — | <0.001 | trace | <0.001 |
| BPX-II | — | trace | trace | trace |
| BPA-HVY | — | 0.001 | trace | 0.001 |
| Spirobi | — | trace | trace | trace |
| IPP | — | <0.001 | trace | <0.001 |

Example 1: Effect of Adding BPA Plant Phenol Recovery Stream 498 to the Splitter Inlet Stream 303

Simulations of the splitter column 320 were performed with no flow from the BPA plant phenol recovery stream 498 (Table 1), and with a 2 gallon per minute (gal/min) (7.5 liters per minute (L/min)) flow from the BPA plant phenol recovery stream 498 combined with the splitter inlet stream 303 (Table 2). The results of the simulations indicate that non-phenol compounds present in the BPA plant phenol recovery stream 498 will pass through the splitter column 320. This result can be beneficial as additional non-phenol compounds from the BPA plant can be separated in the splitter column 320 without impacting the composition of the acetone product stream 231.

TABLE 5

| Condition/Composition | Stream 322 | Stream 498 | Stream 361 | Stream 362 |
|---|---|---|---|---|
| Temperature (K) | 464.2 | 353.1 | 330.7 | 478.7 |
| Pressure (kN/m$^2$) | 160 | 500 | 460 | 294 |
| Vapor Fraction | 0 | 0 | 0 | 0 |
| Mole Flow (kmol/s) | 0.136 | 0.003 | 0.140 | 0.002 |
| Mass Flow (kg/s) | 12.959 | 0.259 | 13.213 | 0.269 |
| Volume Flow (m$^3$/s) | 0.014 | <0.001 | 0.013 | <0.001 |
| Mass Flow (kg/s) | | | | |
| Acetone | — | — | — | — |
| Phenol | 12.687 | 0.254 | 13.212 | 0.040 |
| Cumene | trace | — | — | — |
| α-methylstyrene | trace | — | trace | trace |
| Dimethylbenzyl alcohol | 0.095 | — | trace | 0.047 |
| Water | trace | 0.001 | 0.001 | trace |
| Paracumyl phenol | 0.049 | — | trace | 0.049 |
| Dicumyl phenol | 0.069 | — | <0.001 | 0.069 |
| Hydroxyacetone | trace | — | trace | trace |
| Acetophenone | 0.042 | — | trace | 0.042 |
| Methanol | — | — | — | — |
| Acetaldehyde | — | — | — | — |
| 2-methylbenzofuran | trace | — | trace | trace |
| AMS Dimer | 0.018 | — | trace | 0.018 |
| para-para BPA | — | 0.003 | trace | 0.003 |
| ortho-para BPA | — | <0.001 | trace | <0.001 |
| Chroman | — | <0.001 | trace | <0.001 |
| Dimers | — | <0.001 | trace | <0.001 |
| BPX-I | — | <0.001 | trace | <0.001 |
| BPX-II | — | <0.001 | trace | <0.001 |
| BPA-HVY | — | 0.001 | trace | 0.001 |
| Spirobi | — | <0.001 | trace | <0.001 |
| IPP | — | <0.001 | trace | <0.001 |

Example 2: Effect of Adding BPA Plant Phenol Recovery Stream 498 to the Splitter Outlet Bottom Stream 322

Simulations of the crude phenol column 360 were performed with some recycle flow from the finisher bottom outlet stream 382 and with no flow from the BPA plant phenol recovery stream 498 (Table 3), with a 2 gal/min (7.6 L/min) flow from the BPA plant phenol recovery stream 498 combined with splitter bottom outlet stream 322 to form a crude phenol inlet stream (Table 4), with a 4 gal/min (15.1 L/min) flow from the BPA plant phenol recovery stream 498 combined with splitter bottom outlet stream 322 to form a crude phenol inlet stream (Table 5), and with a 6 gal/min (22.7 L/min) flow from the BPA plant phenol recovery stream 498 combined with splitter bottom outlet stream 322 to form a crude phenol inlet stream (Table 6). The result of these simulations indicate that non-phenol compounds present in the BPA plant phenol recovery stream 498 can be removed through the bottoms of the crude phenol column 360 and the resultant overhead stream (crude top outlet stream 361) can be unaffected by the added process stream.

TABLE 6

| Condition/Composition | Stream 322 | Stream 498 | Stream 361 | Stream 362 |
|---|---|---|---|---|
| Temperature (K) | 464.2 | 353.1 | 330.7 | 478.9 |
| Pressure (kN/m$^2$) | 160 | 500 | 460 | 294 |
| Vapor Fraction | 0 | 0 | 0 | 0 |
| Mole Flow (kmol/s) | 0.136 | 0.004 | 0.142 | 0.002 |
| Mass Flow (kg/s) | 12.959 | 0.389 | 13.343 | 0.271 |
| Volume Flow (m$^3$/s) | 0.014 | <0.001 | 0.013 | <0.001 |
| Mass Flow (kg/s) | | | | |
| Acetone | — | — | — | — |
| Phenol | 12.687 | 0.381 | 13.341 | 0.041 |
| Cumene | trace | — | | |
| α-methylstyrene | trace | — | trace | trace |
| Dimethylbenzyl alcohol | 0.095 | — | trace | 0.046 |
| Water | trace | 0.001 | 0.001 | trace |
| Paracumyl phenol | 0.049 | — | trace | 0.049 |
| Dicumyl phenol | 0.069 | — | <0.001 | 0.069 |
| Hydroxyacetone | trace | — | trace | trace |
| Acetophenone | 0.042 | — | trace | 0.042 |
| Methanol | — | — | — | — |
| Acetaldehyde | — | — | — | — |
| 2-methylbenzofuran | trace | — | trace | trace |
| AMS Dimer | 0.018 | — | trace | 0.018 |
| para-para BPA | — | 0.004 | trace | 0.004 |
| ortho-para BPA | — | <0.001 | trace | <0.001 |
| Chroman | — | <0.001 | trace | trace |

TABLE 6-continued

| Condition/Composition | Stream 322 | Stream 498 | Stream 361 | Stream 362 |
|---|---|---|---|---|
| Dimers | — | <0.001 | trace | <0.001 |
| BPX-I | — | <0.001 | trace | <0.001 |
| BPX-II | — | <0.001 | trace | <0.001 |
| BPA-HVY | — | 0.002 | trace | 0.002 |
| Spirobi | — | <0.001 | trace | <0.001 |
| IPP | — | <0.001 | trace | <0.001 |

Example 3: Effect of Adding BPA Plant Phenol Recovery Stream 498 to the Crude Top Outlet Stream 361

Simulations of the hydro-extractor column 370 were performed with no flow from the BPA plant phenol recovery stream 498 (Table 7), and with a 2 gal/min (7.6 L/min) flow from the BPA plant phenol recovery stream 498 combined with the crude top outlet stream 361 (Table 8). The results of these simulations indicate that non-phenol compounds present in the BPA plant phenol recovery stream 498 can affect the composition of the product phenol outlet stream 381.

TABLE 7

| Condition/Composition | Stream 361 | Stream 373 | Stream 371 |
|---|---|---|---|
| Temperature (K) | 330.7 | 358.1 | 489.2 |
| Pressure (kN/m$^2$) | 460 | 105 | 239 |
| Vapor Fraction | 0 | 0 | 0 |
| Mole Flow (kmol/s) | 0.138 | 0.046 | 0.142 |
| Mass Flow (kg/s) | 12.953 | 0.820 | 13.318 |
| Volume Flow (m$^3$/s) | 0.012 | 0.001 | 0.015 |
| Mass Flow (kg/s) | | | |
| Acetone | — | — | — |
| Phenol | 12.953 | — | 13.317 |
| Cumene | — | — | — |
| α-methylstyrene | trace | — | trace |
| Dimethylbenzyl alcohol | trace | — | trace |
| Water | trace | 0.820 | trace |
| Paracumyl phenol | — | — | — |
| Dicumyl phenol | <0.001 | — | <0.001 |
| Hydroxyacetone | trace | — | trace |
| Acetophenone | trace | — | trace |
| Methanol | — | — | — |
| Acetaldehyde | — | — | — |
| 2-methylbenzofuran | trace | — | <0.001 |
| AMS Dimer | — | — | — |

Set forth below are embodiments of the method of recovering phenol in a BPA production plant and the plant for recovering the same.

Embodiment 1

A method of recovering phenol from a bisphenol A production facility comprising: reacting phenol and acetone in the presence of a catalyst to produce a bisphenol A stream comprising bisphenol A; separating the bisphenol A stream into a product bisphenol A stream and a purge stream comprising an unreacted phenol; separating the purge stream into a primary top outlet stream and a primary bottom outlet stream in a primary distillation column; adding an acid catalyst via acid stream to the primary bottom outlet stream to form a cracker inlet stream; separating the cracker inlet stream into a cracker top outlet stream and a cracker bottom outlet stream in the acid-cracker; separating the cracker top outlet stream and the cracker bottom outlet stream into a secondary top outlet stream and a secondary bottom outlet stream in a secondary recovery column; forming a bisphenol A plant phenol recovery stream comprising at least a portion of the primary top outlet stream, at least a portion of the cracker top outlet stream, at least a portion of the secondary top outlet stream, or a combination comprising at least one of the foregoing; combining the bisphenol A plant phenol recovery stream with a stream of a phenol purification plant selected from a preheater inlet stream, a splitter inlet stream, a splitter bottom outlet stream, a crude top outlet stream, or a combination comprising at least one of the foregoing.

TABLE 8

| Condition/Composition | Stream 361 | Stream 498 | Stream 373 | Stream 371 |
|---|---|---|---|---|
| Temperature (K) | 330.7 | 353.1 | 358.1 | 489.2 |
| Pressure (kN/m$^2$) | 460 | 500 | 105 | 239 |
| Vapor Fraction | 0 | 0 | 0 | 0 |
| Mole Flow (kmol/s) | 0.138 | 0.001 | 0.046 | 0.143 |
| Mass Flow (kg/s) | 12.953 | 0.130 | 0.820 | 13.452 |
| Volume Flow (m$^3$/s) | 0.012 | <0.001 | 0.001 | 0.015 |
| Mass Flow (kg/s) | | | | |
| Acetone | — | — | — | — |
| Phenol | 12.953 | 0.127 | — | 13.450 |
| Cumene | — | — | — | — |
| α-methylstyrene | trace | — | — | trace |
| Dimethylbenzyl alcohol | trace | — | — | trace |
| Water | trace | <0.001 | 0.820 | trace |
| Paracumyl phenol | — | — | — | — |
| Dicumyl phenol | <0.001 | — | — | <0.001 |
| Hydroxyacetone | trace | — | — | trace |
| Acetophenone | trace | — | — | trace |
| Methanol | — | — | — | — |
| Acetaldehyde | — | — | — | — |
| 2-methylbenzofuran | trace | — | — | trace |
| AMS Dimer | — | — | — | — |
| para-para BPA | trace | 0.001 | — | 0.001 |
| ortho-para BPA | trace | <0.001 | — | <0.001 |
| Chroman | trace | <0.001 | — | <0.001 |
| Dimers | trace | <0.001 | — | <0.001 |
| BPX-I | trace | <0.001 | — | <0.001 |
| BPX-II | trace | trace | — | trace |
| BPA-HVY | trace | 0.001 | — | 0.001 |
| Spirobi | trace | trace | — | trace |
| IPP | trace | <0.001 | — | <0.001 |

Embodiment 2

The method of Embodiment 1, wherein combining comprises combining the bisphenol-A plant phenol recovery stream with the splitter bottom outlet stream.

Embodiment 3

The method of any one of the preceding embodiments, wherein combining comprises combining the bisphenol-A plant phenol recovery stream with crude top outlet stream.

Embodiment 4

The method of any one of the preceding embodiments, further comprising adding a cracker recycle stream from the acid-cracker to the primary distillation column.

Embodiment 5

The method of any one of the preceding embodiments, wherein the primary distillation column operates at one or both of a temperature of 60 to 200° C., specifically, 75 to 110° C. and a pressure of 1 to 10 kPa, specifically, 2 to 8 kPa.

Embodiment 6

The method of any one of the preceding embodiments, wherein the cracker top outlet stream comprises 95 to 99 wt % phenol, specifically, 97 to 99 wt % of phenol.

Embodiment 7

The method of any one of the preceding embodiments, wherein the acid-cracker operates at one or both of a temperature of 100 to 200° C., specifically, 130 to 180° C. and a pressure of 5 to 50 kPa, specifically, 10 to 30 kPa.

Embodiment 8

The method of any one of the preceding embodiments, wherein the secondary top outlet stream comprises 95 to 99 wt % phenol.

Embodiment 9

A method of recovering phenol comprising: heating a preheater inlet stream comprising cumene, phenol, and acetone in a preheater to form a splitter inlet stream; separating the splitter inlet stream comprising the cumene, the phenol, and the acetone into a splitter top outlet stream comprising the acetone and the cumene and a splitter bottom outlet stream comprising the phenol in a splitter column; separating the splitter bottom outlet stream into a crude top outlet stream comprising the phenol and a crude bottom outlet stream comprising the cumene in a crude phenol column; hydro-extracting the crude top outlet stream in a hydro-extractor column to form an extractor primary outlet stream comprising the phenol; recovering a product phenol outlet stream, comprising the phenol in a concentration of greater than 99.5 wt % based on the total weight of the product phenol outlet stream, from the extractor primary outlet stream in a finishing column; combining a bisphenol A plant phenol recovery stream from a bisphenol A reaction comprising 95 to 99 wt % of a recovered phenol from a bisphenol A phenol purification system with the preheater inlet stream, the splitter inlet stream, the splitter bottom outlet stream, the crude top outlet stream, or a combination comprising at least one of the foregoing.

Embodiment 10

The method of Embodiment 9, wherein the combining comprises combining the bisphenol A plant phenol recovery stream from the bisphenol A phenol purification system with the preheater inlet stream, the splitter inlet stream, the splitter bottom outlet stream, or a combination comprising at least one of the foregoing.

Embodiment 11

The method of any one of Embodiments 9-10, wherein the product phenol outlet stream comprises less than or equal to 0.001 wt % of water, cumene, dimethylbenzyl alcohol (DMBA), hydroxyacetone (HA), α-methylstyrene (AMS), AMS dimers, acetophenone (AP), acetaldehyde, cumyl phenols, and phenolic resins based on the total weight of the product phenol outlet stream.

Embodiment 12

The method of any one of Embodiments 9-11, further comprising ion-exchanging the extractor primary outlet stream in an ion-exchanger prior to recovering the product phenol outlet stream.

Embodiment 13

The method of any one of Embodiments 9-12, further comprising adding a finisher bottom outlet stream that is separated in the finishing column to the crude phenol column.

Embodiment 14

The method of any one of Embodiments 9-13, further comprising cooling an extractor outlet top stream in a cooler from the hydro-extractor to form a cooled stream and adding the cooled stream back into the hydro-extractor column, and further comprising adding a water stream into the cooler.

Embodiment 15

The method of any one of Embodiments 9-14, further comprising an acetone purification system, wherein the acetone purification system produces an acetone product stream and an acetone purification recycle stream and wherein the method further comprises adding the splitter top outlet stream to the acetone purification system. Optionally, the acetone product stream can comprise greater than or equal to 95 wt % acetone, for example, 95 to 100 wt %, or, 97 to 99.99 wt %.

Embodiment 16

The method of Embodiment 15, further comprising adding the acetone purification recycle stream to the preheater.

Embodiment 17

The method of any one of Embodiments 9-16, wherein the splitter column operates at one or both of a temperature of 90 to 150° C., specifically, 100 to 140° C. and a pressure of 250 to 450 kilopascal (kPa), specifically, 300 to 400 kPa.

Embodiment 18

The method of any one of Embodiments 9-17, wherein the splitter top outlet stream comprises one or more of 30 to 70 wt %, specifically, 40 to 60 wt % of acetone; 0 to 5 wt %, specifically, 0 to 1 wt % phenol; and 30 to 70 wt %, specifically, 40 to 60 wt % of non-phenol compounds.

Embodiment 19

The method of any one of Embodiments 9-18, wherein the crude phenol column operates at one or both of a temperature of 100 to 300° C., specifically, 150 to 250° C. and a pressure of 75 to 275 kPa, specifically, 100 to 225 kPa.

Embodiment 20

The method of any one of Embodiments 9-19, wherein the crude bottom outlet stream comprises 97 to 99.7 wt % of phenol.

Embodiment 21

The method of any one of Embodiments 9-20, wherein the hydro-extractor column operates at one or both of a temperature of 30 to 100° C., specifically, 50 to 70° C. and a pressure of 350 to 550 kPa, specifically, 400 to 500 kPa.

Embodiment 22

The method of any one of Embodiments 9-21, wherein the extractor primary outlet stream comprises 98 to 99.999 wt % of phenol.

Embodiment 23

The method of any one of Embodiments 9-22, wherein the product phenol outlet stream comprises greater than or equal to 99.5 wt %, specifically, 99.5 to less than 100 wt % of phenol.

Embodiment 24

The method of any one of the preceding embodiments, wherein the splitter inlet stream comprises 5 to 50 wt %, specifically, 10 to 40 wt %, more specifically, 20 to 30 wt % acetone.

Embodiment 25

The method of any one of the preceding embodiments, wherein the splitter inlet stream comprises 20 to 75 wt %, specifically, 30 to 60 wt %, more specifically 40 to 50 wt % phenol.

Embodiment 26

The method of any one of the preceding embodiments, wherein the splitter inlet stream comprises 0 to 35 wt %, specifically, 5 to 30 wt % of a non-phenol compound.

Embodiment 27

The method of any one of the preceding embodiments, wherein the splitter bottom outlet stream comprises one or more of greater than or equal to 94 wt %, specifically, 95 to 99 wt %, more specifically, 97 to 99 wt % of phenol; 0 to 4 wt % of α-methylstyrene; 0 to 2 wt % of acetophenone; and 0 to 1 wt % of each of the following independently: acetone, cumene, α-methylstyrene, water, dimethylbenzyl alcohol, paracumyl phenol, dicumyl phenol, hydroxyacetone, acetophenone, methanol, acetaldehyde, 2-methylbenzofuran, and AMS dimers.

Embodiment 28

A system for recovering phenol comprising: a phenol purification system and a bisphenol A production facility. The phenol purification system comprises a preheater, a splitter column, a crude phenol column, a hydro-extractor column, and a finishing column. The preheater comprises a preheater inlet and a preheater outlet. The splitter column comprises a splitter inlet in fluid communication with the preheater outlet, a splitter top outlet, and a splitter bottom outlet. The crude phenol column comprises a crude inlet in fluid communication with the splitter bottom outlet, a crude top outlet, and a crude bottom outlet. The hydro-extractor column comprises an extractor inlet in fluid communication with the crude top outlet, an extractor outlet, and an extractor primary outlet. The finishing column comprises a finisher inlet in fluid communication with the extractor primary outlet, a product phenol outlet, and a finisher bottom outlet. The bisphenol A production facility comprises a bisphenol A reactor, a bisphenol A separation unit, a primary distillation column, an acid-cracker, and a secondary recovery column. The bisphenol A reactor comprises a reactor inlet and a reactor outlet. The bisphenol A separation unit comprises a bisphenol A separation inlet in fluid communication with the reactor outlet, a bisphenol A separation first outlet, and a bisphenol A separation second outlet. The primary distillation column comprises a primary inlet in fluid communication with the bisphenol A separation first outlet, a primary top outlet, and a primary bottom outlet. The acid-cracker comprises a cracker inlet in fluid communication with the primary bottom outlet, a cracker top outlet, and a cracker bottom outlet. The secondary recovery column comprises a first inlet in fluid communication with the cracker top outlet, a second inlet in fluid communication with the cracker bottom outlet, a secondary top outlet, and a secondary bottom outlet. The primary top outlet, the cracker top outlet, the secondary top outlet, or a combination comprising at least one of the foregoing is in fluid communication with the preheater inlet, the splitter inlet, the crude inlet, the extractor inlet, or a combination comprising at least one of the foregoing. The system can be used in the methods of any of one Embodiments 1-27.

Embodiment 29

The system of Embodiment 28, wherein the primary top outlet, the cracker top outlet, the secondary top outlet, or a combination comprising at least one of the foregoing is in fluid communication with the preheater inlet.

Embodiment 30

The system of any one of Embodiments 28-29, wherein the primary top outlet, the cracker top outlet, the secondary top outlet, or a combination comprising at least one of the foregoing, is in fluid communication with the splitter inlet.

Embodiment 31

The system of any one of Embodiments 28-30, wherein the primary top outlet, the cracker top outlet, the secondary top outlet, or a combination comprising at least one of the foregoing, is in fluid communication with the crude inlet.

Embodiment 32

The system of any one of Embodiments 28-31, wherein the primary top outlet, the cracker top outlet, the secondary top outlet, or a combination comprising at least one of the foregoing, is in fluid communication with the extractor inlet.

Embodiment 33

The system of any one of Embodiments 28-32, further comprising an ion exchanger comprising an exchanger inlet in fluid communication with the extractor primary outlet and an exchanger outlet in fluid communication with the finisher inlet.

Embodiment 34

The system of any one of Embodiments 28-33, wherein the finisher bottom outlet is in fluid communication with the crude inlet.

Embodiment 35

The system of any one of Embodiments 28-34, wherein the acid-cracker further comprises a cracker recycle outlet and the primary distillation column further comprises a primary recycle inlet, and wherein the cracker recycle outlet is in fluid communication with the primary recycle inlet.

Embodiment 36

The system of any one of Embodiments 28-35, further comprising a cooler comprising a cooler inlet and a cooler outlet, wherein the cooler inlet is in fluid communication with the extractor outlet and wherein the cooler outlet is in fluid communication with a cooler extractor inlet of the hydro-extractor column.

Embodiment 37

The system of any one of Embodiments 28-36, further comprising an acetone purification system wherein the splitter top outlet is in fluid communication with the acetone purification system.

Embodiment 38

The system of any one of Embodiments 28-37, further comprising an acetone purification system wherein the preheater inlet is in fluid communication with the acetone purification system.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt %, or, more specifically, 5 wt % to 20 wt %", is inclusive of the endpoints and all intermediate values of the ranges of "5 wt % to 25 wt %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to Applicants or others skilled in the art. Accordingly, the appended claims as filed and as they may be amended are intended to embrace all such alternatives, modifications variations, improvements, and substantial equivalents.

We claim:

1. A method of recovering phenol comprising:
   heating a preheater inlet stream comprising cumene, phenol, and acetone in a preheater to form a splitter inlet stream;
   separating the splitter inlet stream comprising the cumene, the phenol, and the acetone into a splitter top outlet stream comprising the acetone and the cumene and a splitter bottom outlet stream comprising the phenol in a splitter column;
   separating the splitter bottom outlet stream into a crude top outlet stream comprising the phenol and a crude bottom outlet stream comprising the cumene in a crude phenol column;
   hydro-extracting the crude top outlet stream in a hydro-extractor column to form an extractor primary outlet stream comprising the phenol;
   recovering a product phenol outlet stream, comprising the phenol in a concentration of greater than 99.5 wt % based on the total weight of the product phenol outlet stream, from the extractor primary outlet stream in a finishing column;
   combining a bisphenol A plant phenol recovery stream from a bisphenol A reaction comprising 95 to 99 wt % of a recovered phenol from a bisphenol A phenol purification system with the preheater inlet stream, the splitter inlet stream, the splitter bottom outlet stream, the crude top outlet stream, or a combination comprising at least one of the foregoing.

2. The method of claim 1, wherein the combining comprises combining the bisphenol A plant phenol recovery stream from the bisphenol A phenol purification system with the preheater inlet stream, the splitter inlet stream, the splitter bottom outlet stream, or a combination comprising at least one of the foregoing.

3. The method of claim 1, wherein the product phenol outlet stream comprises less than or equal to 0.001 wt % of water, cumene, dimethylbenzyl alcohol (DMBA), hydroxyacetone (HA), α-methylstyrene (AMS), AMS dimers, acetophenone (AP), acetaldehyde, cumyl phenols, and phenolic resins based on a total weight of the product phenol outlet stream.

4. The method of claim 1, further comprising ion-exchanging the extractor primary outlet stream in an ion-exchanger prior to recovering the product phenol outlet stream.

5. The method of claim 1, further comprising adding a finisher bottom outlet stream that is separated in the finishing column to the crude phenol column.

6. The method of claim 1, further comprising cooling an extractor outlet top stream in a cooler from the hydro-extractor to form a cooled stream and adding the cooled stream back into the hydro-extractor column, and further comprising adding a water stream into the cooler.

7. The method of claim 1, further comprising an acetone purification system, wherein the acetone purification system produces an acetone product stream and an acetone purification recycle stream and wherein the method further comprises adding the splitter top outlet stream to the acetone purification system.

8. The method of claim 7, further comprising adding the acetone purification recycle stream to the preheater.

9. A system for recovering phenol comprising:
a phenol purification system comprising
a preheater comprising a preheater inlet and a preheater outlet,
a splitter column comprising a splitter inlet in fluid communication with the preheater outlet, a splitter top outlet, and a splitter bottom outlet,
a crude phenol column comprising a crude inlet in fluid communication with the splitter bottom outlet, a crude top outlet, and a crude bottom outlet,
a hydro-extractor column comprising an extractor inlet in fluid communication with the crude top outlet, an extractor outlet, and an extractor primary outlet, and
a finishing column comprising a finisher inlet in fluid communication with the extractor primary outlet, a product phenol outlet, and a finisher bottom outlet; and
a bisphenol A production facility comprising
a bisphenol A reactor comprising a reactor inlet and a reactor outlet;
a bisphenol A separation unit comprising a bisphenol A separation inlet in fluid communication with the reactor outlet, a bisphenol A separation first outlet, and a bisphenol A separation second outlet;
a primary distillation column comprising a primary inlet in fluid communication with the bisphenol A separation first outlet, a primary top outlet, and a primary bottom outlet,
an acid-cracker comprising a cracker inlet in fluid communication with the primary bottom outlet, a cracker top outlet, and a cracker bottom outlet, and
a secondary recovery column comprising a first inlet in fluid communication with the cracker top outlet, a second inlet in fluid communication with the cracker bottom outlet, a secondary top outlet, and a secondary bottom outlet; and
wherein the primary top outlet, the cracker top outlet, the secondary top outlet, or a combination comprising at least one of the foregoing is in fluid communication with the preheater inlet, the splitter inlet, the crude inlet, the extractor inlet, or a combination comprising at least one of the foregoing.

10. The system of claim 9, wherein the primary top outlet, the cracker top outlet, the secondary top outlet, or a combination comprising at least one of the foregoing is in fluid communication with the preheater inlet and/or wherein the primary top outlet, the cracker top outlet, the secondary top outlet, or a combination comprising at least one of the foregoing, is in fluid communication with the splitter inlet.

11. The system of claim 9, wherein the primary top outlet, the cracker top outlet, the secondary top outlet, or a combination comprising at least one of the foregoing, is in fluid communication with the crude inlet and/or wherein the primary top outlet, the cracker top outlet, the secondary top outlet, or a combination comprising at least one of the foregoing, is in fluid communication with the extractor inlet.

12. The system of claim 9, further comprising an ion exchanger comprising an exchanger inlet in fluid communication with the extractor primary outlet and an exchanger outlet in fluid communication with the finisher inlet.

13. The system of claim 9, wherein the finisher bottom outlet is in fluid communication with the crude inlet.

14. The system of claim 9, wherein the acid-cracker further comprises a cracker recycle outlet and the primary distillation column further comprises a primary recycle inlet, and wherein the cracker recycle outlet is in fluid communication with the primary recycle inlet.

15. The system of claim 9, further comprising a cooler comprising a cooler inlet and a cooler outlet, wherein the cooler inlet is in fluid communication with the extractor outlet and wherein the cooler outlet is in fluid communication with a cooler extractor inlet of the hydro-extractor column.

16. The system of claim 9, further comprising an acetone purification system wherein the splitter top outlet is in fluid communication with the acetone purification system and/or further comprising the acetone purification system wherein the preheater inlet is in fluid communication with the acetone purification system.

* * * * *